US005451622A

United States Patent [19]

Boardman et al.

[11] Patent Number: 5,451,622
[45] Date of Patent: Sep. 19, 1995

[54] COMPOSITION COMPRISING THERMOPLASTIC POLYMER AND FLUOROCHEMICAL PIPERAZINE COMPOUND

[75] Inventors: Gail S. Boardman; Richard S. Buckanin, both of Woodbury, Minn.

[73] Assignee: Minnesota Mining and Manufacturing Company, St. Paul, Minn.

[21] Appl. No.: 954,249

[22] Filed: Sep. 30, 1992

[51] Int. Cl.⁶ .......................................... C08K 5/3492
[52] U.S. Cl. ..................................................... 524/100
[58] Field of Search ........................ 524/100; 428/288

[56] References Cited

U.S. PATENT DOCUMENTS

| | | | |
|---|---|---|---|
| 2,759,019 | 8/1956 | Brown et al. | 260/556 |
| 3,170,926 | 2/1965 | Ash | 544/392 |
| 3,211,608 | 10/1965 | Maryer et al. | 167/53 |
| 3,394,137 | 7/1968 | Morris | 544/392 |
| 3,899,563 | 8/1975 | Oxenrider et al. | 264/211 |
| 3,954,770 | 5/1976 | Mayerhoefer et al. | 524/100 |
| 4,266,080 | 5/1981 | Falk et al. | 568/45 |
| 4,468,527 | 8/1984 | Patel | 564/96 |
| 5,025,052 | 6/1991 | Crater et al. | 524/104 |

FOREIGN PATENT DOCUMENTS

| | | |
|---|---|---|
| 1604039 | of 0000 | France . |
| WO93/07914 | of 0000 | WIPO . |
| 9218569 | 10/1992 | WIPO . |

OTHER PUBLICATIONS

Banks, Ed., Organofluorine Chemicals and Their Industrial Applications, Ellis Horwood Ltd., Chichester England, 1979, pp. 226–234.

Mares, F., et al., "Modification of Fiber Surfaces by Monomeric Additives, Part I: Extrusion Techniques," Textile Research Journal, vol. 47, No. 8, pp. 551–561.

Mares, F., et al., "Modification of Fiber Surfaces by Monomeric Additives, Part II: Absorption of Fluorocarbon Additives by Polyethylene Terephthalate," Textile Research Journal, vol. 48, No. 4, pp. 3218–3229.

Katritzky et al., "Design and Synthesis of Novel Fluorinated Surfactants for Hydrocarbon Subphases," Langmuir, vol. 4, (No. 3), pp. 732–735 (1988).

"Estimation of the Surface Free Energy of Polymers," Journal of Applied Polymer Science, vol. 13, pp. 174–177 (1969).

*Primary Examiner*—Kriellion S. Morgan
*Attorney, Agent, or Firm*—Gary L. Griswold; Walter N. Kirn; Robert H. Brink

[57] ABSTRACT

Mixtures comprising thermoplastic polymer, such as polypropylene, and fluorochemical piperazine are provided. Shaped articles, such as fibers, made from these mixtures have low surface-energy surfaces which results in oil- and water-repellency and anti-soiling properties.

18 Claims, No Drawings

COMPOSITION COMPRISING THERMOPLASTIC POLYMER AND FLUOROCHEMICAL PIPERAZINE COMPOUND

This invention relates to the use of fluorochemical compositions to impart water and oil repellency to shaped articles, such as fibers and films. In another aspect it relates to thermoplastic mixtures of fluorochemical and thermoplastic polymer, such as polypropylene, and to the shaped articles thereof, such as fibers and films.

The use of various fluoroaliphatic radical-containing substances, e.g. Scotchgard ™ carpet protector on fibers and fibrous substrates, such as textiles, paper, and leather, to impart oil and water repellency, is known. See, for example, Banks, Ed., *Organofluorine Chemicals and Their Industrial Applications*, Ellis Horwood Ltd., Chichester England, 1979, pp. 226–234. Such fluoroaliphatic radical-containing substances include, for example, fluoroaliphatic radical-containing alcohols (U.S. Pat. No. 4,468,527, Patel), fluoroaliphatic radical-containing amines (U.S. Pat. No. 2,759,019, Brown et al.), and fluoroaliphatic radical-containing oxazolidinones (U.S. Pat. No. 5,025,052, Crater et al.).

Various fluoroaliphatic radical-containing compositions can be applied to various fibrous substrates, such as carpet, by methods which include, for example, spraying, padding, and finish bath immersion. Certain fluoroaliphatic radical-containing compositions may be used as melt additives by melt extrusion of a blend of a synthetic organic fiber-forming polymer and a fluoroaliphatic radical-containing composition. Such melt extrusion is described, for example, by Mares, F., et al., "Modification of Fiber Surfaces by Monomeric Additives, Part I: Extrusion Techniques" *Textile Research Journal*, Vol. 47, No. 8, pp. 551–61 and Mares, F., et al., "Modification of Fiber Surfaces by Monomeric Additives, Part II: Absorption of Fluorocarbon Additives by Polyethylene Terephthalate", *Textile Research Journal*, Vol. 48, No. 4, pp. 3218–29, and in U.S. Pat. No. 3,899,563 (Oxenrider et al.).

U.S. Pat. No. 5,025,052 (Crater et al.) discloses certain fluorochemical oxazolidinone compositions used as melt additives to prepare thermoplastic fibers and films exhibiting low surface energy.

U.S. Pat. No. 3,211,608 (Maryer et al.) disclosed certain 4-alkyl-piperazine-sulfonamides where the sulfur atom of the sulfonamide is bonded to one of the nitrogen atoms of a piperazine ring. These sulfonamides are said to possess valuable pharamacological properties.

U.S. Pat. No. 3,170,926 (Ash et al.) disclosed certain N-phenylpiperazine compounds. Included in the disclosure are compounds where the phenyl substituent is a trifluoromethylphenyl substituent. These compounds are said to have therapeutic value.

Certain N-1(perfluorooctanesulfonyl) piperazine compounds are described in Katritzky et al., "Design and Synthesis of Novel Fluorinated Surfactants for Hydrocarbon Subphases," *Langmuir*, Vol 4 (No. 3), pp 732–735, (1988). Some of these compounds are said to show surface activity in diesel fuel.

Briefly, in one aspect, the present invention provides a thermoplastic composition comprising a fluoroaliphatic radical-containing piperazine compound and thermoplastic synthetic organic polymer, such as polyamide, polyurethane, polyester, and polyolefin, e.g. polypropylene. The thermoplastic composition can be melted and shaped, for example by extrusion or molding, to produce shaped articles, such as fibers and films. Said fluoroaliphatic radical-containing piperazine compound imparts desirable oil-and water-repellencies to the surfaces of said shaped articles.

Fluoroaliphatic radical-containing piperazine compounds useful in the present invention comprise a fluoroaliphatic moiety and a piperazine ring. A class of said piperazine compounds are those that further comprise an organic moiety, and where one of the nitrogen atoms of said piperazine ring is bonded to said fluoroaliphatic moiety through a linking group, and the other nitrogen atom of said piperazine ring is bonded to said organic moiety. The fluoroaliphatic moiety comprises at least two, preferably at least five, fully-fluorinated, saturated aliphatic carbon atoms which are preferably in a chain that can be straight (normal) chain or branched chain, e.g., —(CF$_2$)$_3$— or —CF(CF$_3$)CF$_2$—, or cyclic or part of a cyclic chain. At the melting point of the polymer, said fluoroaliphatic radical-containing piperazines preferably are meltable, non-volatile, compatible with the thermoplastic polymer, and non-reactive with the thermoplastic polymer.

This invention also provides shaped articles such as pellets, fibers, and films prepared, for example, by melt extrusion, and molded articles prepared, for example, by injection molding the mixtures of the present invention. The resulting pellets, fibers, films, etc. have low surface-energy surfaces which results in oil-and water-repellency and anti-soiling properties.

A class of the fluoroaliphatic radical-containing piperazine compounds useful in this invention can be represented by Formula I.

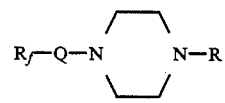

I

In Formula I, R$_f$ is a fluoroaliphatic group or radical, which is a fluorinated, monovalent, saturated aliphatic radical of at least two, preferably at least five, fully-fluorinated carbon atoms. It can be straight chain, branched chain, or, if sufficiently large, cyclic, or combinations thereof, such as alkylcycloaliphatic radicals. The skeletal chain in the fluoroaliphatic group can include catenary oxygen, hexavalent sulfur, and/or trivalent nitrogen hetero atoms bonded only to carbon atoms of the skeletal chain, such hetero atoms providing stable linkages between fluorocarbon portions of the R$_f$ group. While R$_f$ can have a large number of carbon atoms, compounds where R$_f$ has up to 20 carbon atoms will be adequate and preferred since large R$_f$ groups usually represent a less efficient utilization of fluorine than is possible with smaller R$_f$ groups. Generally R$_f$ will have 3 to 20 carbon atoms, preferably 6 to about 12, and will contain 40 to 78 weight percent, preferably 50 to 78 weight percent, fluorine. The terminal portion of the R$_f$ group is a perfluorinated moiety which will preferably contain at least 7 fluorine atoms, e.g., CF$_3$CF$_2$CF$_2$—, F$_5$SCF$_2$, or the like. The preferred compounds are those in which the R$_f$ group is fully or substantially completely fluorinated, as in the case where R$_f$ is perfluoroalkyl, e.g. CF$_3$(CF$_2$)$_n$—. R$_f$ may have up to 20 carbon atoms and include, for example, C$_8$F$_{17}$—, C$_6$F$_{13}$CH$_2$CH$_2$—, C$_{10}$F$_{21}$CH$_2$CH$_2$—.

The divalent linking group Q in Formula I provides a means to link $R_f$ with the depicted piperazine ring. Q can comprise a hetero atom-containing group, e.g., a group containing —SO$_2$— or an organic group or a combination of such groups, examples of which are aliphatic, e.g., —(CH$_2$)$_n$— where n is 2 to 6, aromatic, oxy, thio, carbonyl, sulfone, sulfoxy, —N(CH$_3$)—, sulfonamide, carbonamido, sulfonamidoalkylene, e.g., —SO$_2$NR(CH$_2$)$_e$, where e is 1 to 6 and R is lower alkyl having 1 to 4 carbon atoms, carbonamidoalkylene, and carbonyloxy. Q is chosen to give a stable linkage to the piperazine ring. The particular Q will also generally depend on the synthetic route used to prepare the fluoroaliphatic radical-containing piperazine compound.

In Formula I, R is an organic group which can contain from 2 to 35 carbon atoms, R preferably contains from 4 to 35 carbon atoms. Particularly preferred R groups comprise a polar group, e.g., hydroxy or carbonyl, located proximal to the piperazine ring, and a non-polar hydrocarbon moiety located distal to the piperazine ring. Said hydrocarbon moiety can be aryl, alkyl, or combinations thereof and can include unsaturation and hetero atoms. Suitable R groups include, for example, —C$_{18}$H$_{37}$
—CH$_2$CH(OH)C$_{16}$H$_{33}$
—C$_{14}$H$_{29}$
—C$_6$H$_5$
—C$_6$H$_4$CH$_3$
—C$_6$H$_4$CH$_2$CH$_3$
—C$_6$H$_3$(CH$_3$)$_2$
—C$_6$H$_2$(CH$_3$)$_3$
—C$_{10}$H$_9$(naphthyl)
—[CH(CH$_3$)CH$_2$]$_n$H
—[CH$_2$CH(CH$_3$)]$_n$H
—[CH(C$_2$H$_5$)CH$_2$]$_n$H
—C(O)N(H)C$_{18}$H$_{37}$
—C(O)C$_{16}$H$_{33}$ Representative fluoroaliphatic radical-containing piperazine compounds useful in the present invention include:

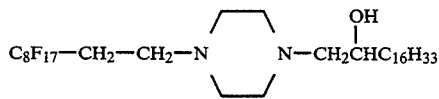

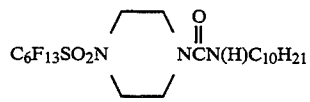

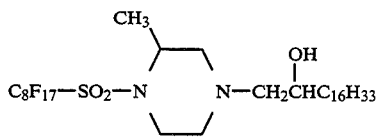

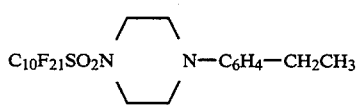

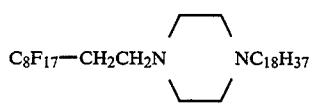

The fluoroaliphatic radical-containing piperazine compounds can be prepared using known organic reactions, such as those disclosed in the Katritzky, et. al. article, supra. A preferred method of preparation is by the reaction of fluoroaliphatic radical-containing sulfonyl fluorides, $R_fSO_2F$, with piperazine,

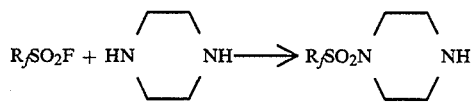

followed by reaction of the resulting fluoroaliphatic radical-containing sulfonylpiperazine with various organic reactants. Representative reaction schemes for the preparation of fluoroaliphatic radical-containing piperazine compounds are outlined below in Schemes A, B, C, and D where $R_f$ and Q are as described above for Formula I and where X is a leaving group such as halogen or tosyl, and R$_1$ together with the rest of the depicted moiety up to but not including the depicted piperazine is R as defined above for Formula I.

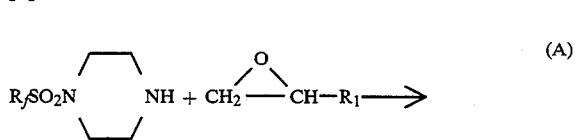

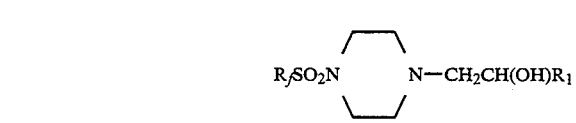

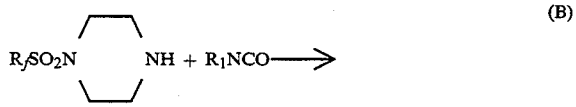

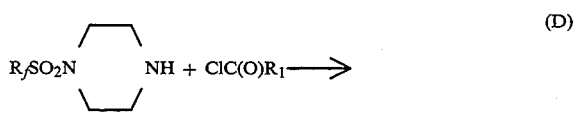

Generally, the fluoroaliphatic radical-containing piperazine compounds useful in this invention will contain about 20 to 70 weight percent, preferably about 25 to 50 weight percent, of carbon-bonded fluorine. If the fluorine content is less than about 20 weight percent, an impractically large amount of the fluoroaliphatic radical-containing compound will generally be required to impart desired oil and water repellencies to the surfaces of resulting shaped articles, while fluorine contents greater than about 70 weight percent are unnecessary to achieve the desired surface properties and thus represent an uneconomical use of fluorine.

Thermoplastic polymers useful in this invention include synthetic linear polyamide, e.g., nylon-6 and nylon-66, polyester, e.g., polyethylene terephthalate, polyurethane, and polyolefin, e.g., polyethylene and polypropylene.

The shaped articles, e.g., fibers and films, of this invention can be made, e.g., by blending or otherwise uniformly mixing the normally solid fluoroaliphatic radical-containing piperazine compound with the solid synthetic polymer, for example by intimately mixing the solid fluoroaliphatic radical-containing piperazine compound with pelletized or powdered polymer, and melt extruding the mixture into shaped articles such as pellets, fibers, or films by known methods. The fluoroaliphatic radical-containing piperazine compound can be mixed per se with the polymer or the fluoroaliphatic radical-containing piperazine compound can be mixed with the polymer in the form of a "masterbatch" (concentrate) of the fluoroaliphatic radical-containing piperazine compound in the polymer. Masterbatches typically contain from about 10% to about 25% by weight of the additive. Also, an organic solution of the fluoroaliphatic radical-containing piperazine compound may be mixed with the powdered or pelletized polymer, the mixture dried to remove solvent, then melted and extruded into the desired shaped article. Alternatively, molten fluoroaliphatic radical-containing piperazine compound (as a compound(s) or masterbatch) can be injected into a molten polymer stream to form a blend just prior to extrusion into the desired shaped article.

In addition to their use in modifying the properties of fibers, e.g., polypropylene carpet fibers, as described above, the fluoroaliphatic radical-containing piperazine compounds are also useful as blend additives to thermoplastic polymer melts from which blown microfibers are made for use in making non-woven fabrics having low surface energy, oil and water repellency and/or soiling resistance.

The amount of fluoroaliphatic radical-containing piperazine compound in the composition is that amount sufficient to produce a shaped article having a surface with the desired properties of oil and water repellency and/or soiling resistance. Preferably, the amount of fluoroaliphatic radical-containing piperazine compound will be that amount which provides from about 100 to 10,000 ppm fluorine, more preferably 200 to 5000 ppm, most preferably 400 to 3000 ppm fluorine, based on the weight of the shaped article.

After melt extrusion of a fiber or film, an annealing step may be carried out to enhance oil and water repellency. This annealing process can be conducted below the melt temperature of the synthetic polymer, for example, in the case of nylon, at about 150° to 220° C. for a period of about 30 seconds to 5 minutes. In some cases, the presence of moisture during annealing, e.g., by using an autoclave to anneal, can improve the effectiveness of the fluoroaliphatic radical-containing piperazine compound.

The following nonlimiting examples are presented to further describe and illustrate the invention.

EXAMPLES

Various fluoroaliphatic radical-containing piperazines were prepared, mixed with thermoplastic polymer, and extruded into fiber. The resulting fiber was knitted into tubular socks or texturized into carpet samples. The oil- and water-repellency of the socks and carpet samples, and the walk-on-soiling resistance of the carpet samples was evaluated.

Water Repellency (WR) Test

The water repellency of socks and carpet samples was measured using a water-isopropyl alcohol test, and is expressed in terms of a water repellency rating of the carpet or socks. Samples which were resistant, i.e. not penetrated by only to 100 percent water, (0 percent isopropyl alcohol) the least penetrating of the test mixtures, were given a rating of 0, (representing the amount of isopropyl alcohol present) whereas samples resistant to 100 percent isopropyl alcohol, the most penetrating of the test mixtures were given a rating of 10. Other intermediate values are determined by use of other water-isopropyl alcohol mixtures. The water repellency rating corresponds to the most penetrating mixture which does not penetrate or wet the sample after 10 seconds contact. If not even resistant to 100% water, the sample was given a rating of F. In general a water repellency rating of 1 (90% water/10% isopropyl alcohol) or better, e.g., 2 (80% water/20% isopropyl alcohol) is desirable for carpet.

Oil Repellency (OR) Test

The oil repellency of socks and carpet samples was measured by AATCC Standard Test 118-1978, which test is based on the resistance of samples to penetration by oils of varying surface tensions. Samples resistant only to Nujol TM mineral oil, and the least penetrating of the test oils, are given a rating of 1, whereas treated fabrics resistant to heptane (the most penetrating of the test oils) are given a value of 8. If not even resistant to Nujol TM mineral oil, the sample was given a rating of F. Other intermediate values are determined by use of other pure oils or mixtures of oils. The rated oil-repellency corresponds to the most penetrating oil (or mixture of oils) which does not penetrate or wet the fabric after 10 seconds contact rather than the 30 seconds contact of the Standard Test. Higher numbers indicate better oil repellency. In general, an oil repellency of 2 or greater is desirable.

Walk-On-Soiling (WOS) Test

The soil resistance of carpet was determined by exposure to pedestrian traffic according to AATCC Test method 122-1979. The exposure site was the corridor (hallway) in a heavily travelled industrial building for an exposure of about 30,000 "traffics" (or one WOS cycle). The samples were repositioned periodically to insure uniform exposure and were vacuumed every 24 hours during the test. After each WOS exposure cycle, i.e. 30,000 "traffics" and before visual evaluation, the carpet samples were vacuumed then subjected to steam cleaning using a Mr. Clean TM carpet steam cleaning machine employing an aqueous cleaning solution prepared from a solution of 4 ounces of STEAMEX TM carpet cleaner in 1 gallon of 49° C. water, passing the machine over the carpet squares first in one direction then once at right angles. The samples were rinsed, using tap water in the steam cleaning machine, then allowed to dry overnight and visually evaluated for degree of soiling as compared to an untreated carpet sample. After rating, additional soiling cycles and ratings were generally done on each carpet sample, including in each case a WOS cycle, vacuuming, steam cleaning, drying and visual rating.

| WOS Rating* | Description |
| --- | --- |
| 0 | equal to control |
| − or + 2 | slightly better (+) or worse (−) than control |
| − or + 4 | significant difference compared to control |
| − or + 6 | very significant difference compared to control |

*Grey scale values multiplied by 4

Rating values vary from −6 to +6 as described, minus (−) values indicating greater soiling than the control, and positive (+) values indicating less soiling than the control, and 0 indicating the same soiling as the control.

Preparation of Socks

Fluoroaliphatic radical-containing piperazine compounds were dry mixed with 12 melt-flow index polypropylene resin pellets in an amount to give the theoretical fluorine-content in the mixture shown in Table 1, and the mixture was extruded as 13.2 denier filaments using a 1.25 inch diameter single screw extruder. The extruder temperatures were 225° C. (zone 1), 230° C. (zone 2), 240° C. (zone 3), and 245° C. (zone 4). The fibers were knit into tubular socks having a circumference of about 17.8 cm using a 10th gauge tubular knitter (Carolina Labknit) from Speizman Industries. The socks were then annealed at a temperature of 135° C. and a relative humidity of 100% for 2 minutes.

Fluorine Content

The fluorine content of each fiber was measured by burn analysis after extrusion.

Preparation of Carpet Samples

Fluoroaliphatic radical-containing piperazine compounds were dry mixed with 12 melt-flow polypropylene resin pellets in an amount to give the theoretical fluorine-content in the mixture shown in Table 2, and the mixture extruded as 13.2 denier filaments using a 1.25 inch diameter single screw extruder. The extruder temperatures were 225° C. (zone 1), 230° C. (zone 3), and 245° C. (zone 4). The fibers were texturized using a Hills air-jet draw-texturizing machine and tufted on a 30.5 cm sample tufter. The carpet samples were then annealed at a temperature of 135° C. and a relative humidity of 100% for 2 minutes.

Example 1

To a 1-L round-bottom flask, equipped with a magnetic stir bar, was added piperazine (Aldrich, anhydrous, 51.7 g, 600 mmol) and dichloromethane (200 mL). With slight cooling of the reaction vessel with a cold water bath, perfluorooctanesulfonyl fluoride (75.3 g, 150 mmol) was added over a 5–10 minute period. The resulting yellow solution was allowed to stir for an additional 2 hr before the addition of ice chips followed by deionized ice cold water. The layers were separated, and the organic layer was washed with two additional portions of deionized water. After drying over anhydrous sodium sulfate, the solvent was removed under reduced pressure. Distillation (0.65–0.70 mm, 140°–142° C., the first cut was discarded) afforded 52.4 g of an off-white solid. Hydrogen and Carbon nuclear magnetic resonance spectra ($^1$H and $^{13}$C NMR), and infrared spectra (IR) data were consistent with the formation of N-(perfluorooctanesulfonyl) piperazine.

To a 500 ml round bottom flask equipped with a magnetic stir bar was added N-(perfluoro-octanesulfonyl)piperazine (19.9g, 35 mmol), 1,2-epoxy-octadecane (85% tech. grade, 11.0 g, 35 mmol) and ethanol (50 ml). This was heated to reflux overnight before removal of the solvent under reduced pressure. The product, an off-white solid, was isolated in quantitative yield. $^1$H and $^{13}$C NMR, and IR data were consistent with the formation of the following compound:

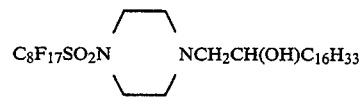

Example 2

N-(perfluorooctanesulfonyl) piperazine was prepared as in Example 1. To a 500 mL round bottom flask equipped with a magnetic stir bar was added N-(perfluorooctanesulfonyl) piperazine (28.4 g, 50 mmol) and ethyl acetate (50 mL). Octadecyl isocyanate (15.0 g, 17.7 mL, 50 mmol) was added slowly with stirring at room temperature. After a couple of minutes, the product began to precipitate from solution and additional ethyl acetate (150 mL) was added to facilitate stirring. To insure complete reaction, the reaction mixture was heated at reflux overnight, and solvent was removed under reduced pressure. The resultant off-white solid (40.7 g, 94%) exhibited $^1$H and $^{13}$C NMR, and IR data consistent with formation of the following compound:

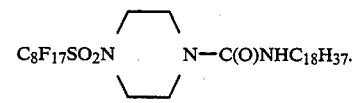

Example 3

Example 3 was prepared as in Example 1 except using perfluorohexanesulfonyl fluoride instead of perfluorooctanesulfonyl fluoride. $^1$H and $^{13}$C NMR, and IR data were consistent with the formation of the following compound:

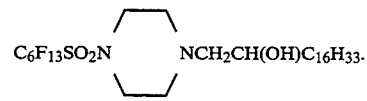

Example 4

Example 4 was prepared as in Example 2 except using the perfluorohexanesulfonyl piperazine of Example 3 instead of the perfluorooctanesulfonyl piperazine of Example 1. $^1$H and $^{13}$C NMR, and IR data were consistent with the formation of the following compound:

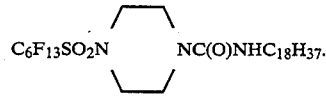

Example 5

To a 250 mL round bottom flask equipped with a magnetic stir bar was added 19.9 g (35 mmole) of the perfluorooctanesulfonyl piperazine of Example 1, 4.25 g (42 mmole) triethylamine, 12.25 g (37 mmole) octadecyl bromide, and 35 mL ethanol. The resulting solution was heated overnight and a tan solid was isolated from the reaction mixture. $^1$H and $^{13}$C NMR, and IR data were consistent with the formation of the following compound:

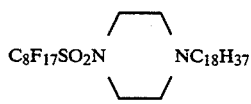

Example 6

Example 6 was prepared as in Example 5, except with stearoyl chloride instead of octadecyl bromide.

To a 500 ml round bottom flask equipped with a magnetic stir bar and a $N_2$ inlet was added N-(Perfluorooctanesulfonyl) piperazine (25.6g, 45 mmol), triethylamine (5.5 g, 7.5 ml, 54 mmol) and $CH_2Cl_2$ (150 ml). A solution of stearoyl chloride (13.6 g, 45 mmol) in $CH_2Cl_2$ (50 ml) was added dropwise to the reaction vessel. After the addition was complete, slight heating was applied to ensure complete reaction. After stirring overnight, the solvent was removed under reduced pressure. The residue was taken up in $CHCl_3$ and washed with three portions of deionized water and one portion of saturated aqueous sodium chloride solution. After drying over anhydrous sodium sulfate, the solvent was removed under solid. $^1H$ and $^{13}C$ NMR, and IR data were consistent with the formation of the following compound

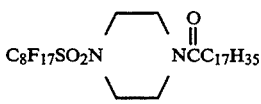

Example 7

Example 7 was prepared as in the preparation of N-(perfluorooctanesulfonyl)piperazine in Example 1, except with twice as much perfluorooctane sulfonyl fluoride. To a 500ml round bottom flask equipped with a magnetic stir bar was added piperazine (8.6 g, 100 mmol), triethylamine (24.3 g, 33.5 ml, 240 mmol) and $CH_2Cl_2$ (200 ml). The perfluorooctanelsulfonylfluoride (100.4 g, 200 mmol) was added neat over 5 min. The yellow reaction mixture was allowed to stir overnight before the addition of deionized water. The aqueous layer was decanted away and the viscous material was washed with an additional three portions of deionized water. The material was allowed to dry to give a yellow solid. $^1H$ and $^{13}C$ NMR, and IR data were consistent with the formulation of the following compound:

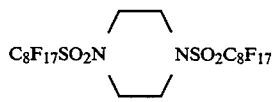

The fluoroaliphatic radical-containing piperazine compounds of Examples 1–7 were mixed with Amoco 5219 polypropylene resin at two concentrations (1500 and 3000 ppm calculated fluorine content) and coextruded at approximately 245° C. to provide fibers which were knitted into socks. A control sample was prepared without fluoroaliphatic radical-containing compound. The data shown in Table I were obtained from testing of these knitted socks and is the average of three samples.

TABLE 1

| Composition of Example | Theoretical Fluorine Content (ppm) | OR | WR |
| --- | --- | --- | --- |
| Control | 0 | F | F |
| 1 | 1500 | 1 | 2 |
|   | 3000 | 4 | 6 |
| 2 | 1500 | 3 | 6 |
|   | 3000 | 3 | 7 |
| 3 | 1500 | F | 1 |
|   | 3000 | 1 | 2 |
| 4 | 1500 | F | 1 |
|   | 3000 | 4 | 5 |
| 5 | 1500 | F | F |
|   | 3000 | F | 2 |
| 6 | 1500 | 1 | 6 |
|   | 3000 | 1 | 7 |
| 7 | 1500 | 0 | F |
|   | 3000 | 0 | F |

The data in Table 1 show that the compositions of this invention have improved oil and water repellency compared to a control sample which does not contain fluorochemical. Particularly preferred compositions are those that contain a piperazine compound that comprises more than 6 fully fluorinated carbon atoms. The compositions containing the piperazine of Example 5 gave lower repellency results, suggesting that the presence of a polar group in the piperazine compound is preferable for good performance. Compositions containing the piperazine of Example 7 gave very low repellency, suggesting that preferred R groups contain a fluorine-free alkyl moiety.

The compositions of the above Examples were mixed with polypropylene, extruded into fiber, and texturized into carpet samples as described above. The amount of the fluoroaliphatic radical-containing composition used was varied to give a theoretical fluorine content of 1500 or 3000 ppm. The oil-repellency, water-repellency, and walk-on-soiling rating for each carpet sample was determined as described above. The data reported in Table 2 is the average of 3 sample. The OR and WR data are reported for the sample before any walk-on cycles(O), and the walk-on-soiling data is shown after the number of cycles shown in Table 2.

TABLE 2

| Composition of Example | Theoretical Fluorine Content (ppm) | Repellency | | Walk-On-Soiling Number of Cycles | | | |
| --- | --- | --- | --- | --- | --- | --- | --- |
|  |  | Oil | Water | 1 | 2 | 3 | 4 |
| 1 | 1500 | 1 | 2 | −1 | +1 | +1 | 0 |
|   | 3000 | 2 | 4 | +1 | +2 | +1 | 0 |
| 2 | 1500 | 2 | 3 | +2 | +3 | +3 | +2 |
|   | 3000 | 2 | 5 | +3 | +5 | +4 | +2 |
| 3 | 1500 | 0 | 0 | +1 | +4 | +1 | +1 |
|   | 3000 | 1 | 2 | +1 | +3 | +1 | 0 |
| 4 | 1500 | 0 | 1 | +2 | +5 | +3 | +2 |
|   | 3000 | 3 | 2 | +2 | +5 | +5 | +2 |
| 5 | 1500 | 0 | F | +1 | +2 | +1 | 0 |
|   | 3000 | 0 | 1 | 0 | +1 | +2 | +1 |
| 6 | 1500 | 1 | 5 | +1 | +1 | 0 | +1 |
|   | 3000 | 1 | 6 | +3 | +2 | +1 | +2 |
| 7 | 1500 | 0 | F | 0 | +2 | +1 | +1 |
|   | 3000 | 0 | F | +2 | +2 | +2 | +1 |

The data in Table 2 show that the compositions of this invention have improved walk-on-soiling resistance compared to a control sample which does not contain fluorochemical. Particularly preferred compositions are those that contain a piperazine compound that comprises a fluorine-free alkyl moiety.

Example 8

Example 8 was prepared as in Example 2 except with 25 mmoles of meta-xylylene diisocyanate instead of 50 mmoles of octadecyl isocyanate. $^1$H and $^{13}$C NMR, and IR data were consistent with the formation of the following compound:

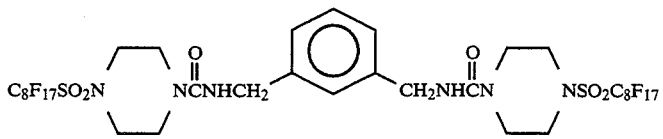

Example 9

Example 9 was prepared as in Example 8 except with methylenediphenyl diisocyanate instead of meta-xylylene diisocyanate. $^1$H and $^{13}$C NMR, and IR data were consistent with the formation of the following compound:

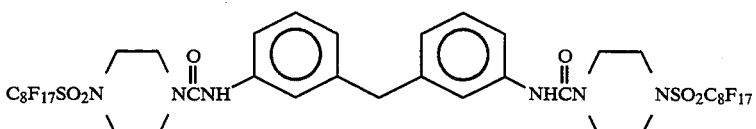

Example 10

Example 10 was prepared as in Example 8 except with toluene diisocyanate instead of metaxylylene diisocyanate. $^1$H and $^{13}$C NMR, and IR data were consistent with the formation of the following compound:

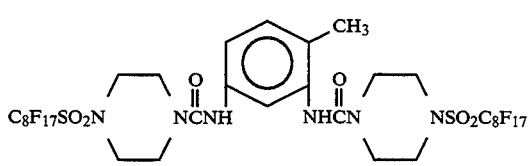

Example 11

Example 11 was prepared as in Example 8 except with isophorone diisocyanate instead of metaxylylene diisocyanate. $^1$H and $^{13}$C NMR, and IR data were consistent with the formulation of the following compound:

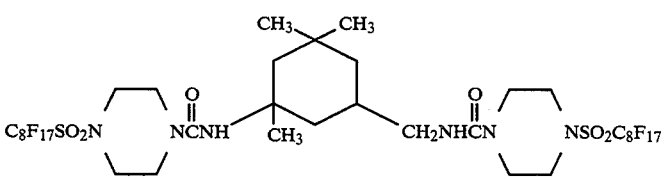

Example 12

Example 12 was prepared as in Example 6 except with adipoyl chloride instead of stearoyl chloride. $^1$H and $^{13}$C NMR, and IR data were consistent with the formation of the following compound:

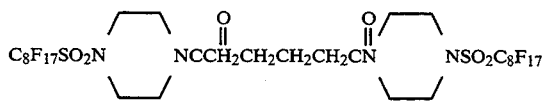

The fluoroaliphatic radical-containing piperazine compounds of Examples 8 to 12 were mixed with nylon-66 polymer in an amount calculated to give the theoretical fluorine content shown in Table 3. A control sample was prepared without fluoroaliphatic radical-containing compound. Nylon 66 films were extruded at thickness of 125 to 250 microns. The surface energy of each film was determined, the results being set forth in Table 3. Surface energy determination for films was made using the contact-angle method set forth in "Estimation of the Surface Free Energy of Polymers", *Journal of Applied Polymer Science*, vol. 13, pp. 174–177 (1969) using Lubinol TM mineral oil (available from Purepac Pharmaceutical Co., a division of Kalipharma, Inc.) and glycerine.

TABLE 3

| Composition of Example | Theoretical Fluorine Content (ppm) | Measured Fluorine Content (ppm) | Surface Energy (dynes/cm) |
|---|---|---|---|
| Control | 0 | — | 35–40 |
| 8 | 2500 | 1550 | 28 |
| 9 | 2500 | 1830 | 26 |
| 10 | 2500 | 1518 | 27 |
| 11 | 2500 | 1565 | 24 |
| 12 | 2500 | 1624 | 25 |

The data in Table 3 show that compositions containing fluoroaliphatic radical-containing piperazines have significantly lower surface-energy than the fluorine-free control.

The various modifications and alterations of this invention will be apparent to those skilled in the art without departing from the scope and spirit of this invention and this invention should not be restricted to that set forth herein for illustrative purposes.

What is claimed is:

1. A composition comprising fluoroaliphatic radical-containing piperazine compound and thermoplastic synthetic organic polymer wherein said fluoroaliphatic radical-containing piperazine compound is

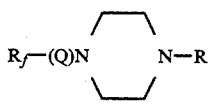

where $R_f$ is a fluorinated, monovalent, saturated aliphatic radical of at least two fully fluorinated carbon atoms; Q is a divalent linking group; and R is an organic moiety comprising from 4 to 35 carbon atoms.

2. The composition of claim 1 wherein said Q is selected from the group consisting of —$(CH_2)_n$— where n is from 2 to 6, —CO—, —$SO_2$—.

3. The composition of claim 1 wherein said Q is selected from the group consisting of —$SO_2$—, —$SO_2N(CH_3)CH_2CH_2$—, —$SO_2N(CH_2CH_3)CH_2CH_2$—, and —$CH_2CH_2$—; said $R_f$ is $C_nF_{2n+1}$ where n is from 5 to 20; and said R comprises a polar group and a non-polar group comprising an aryl moiety, alkyl moiety, or combinations thereof.

4. The composition of claim 3 wherein said R comprises a polar group and an alkyl group of formula $C_yH_{2y+1}$ where y is from 4 to 20.

5. The composition of claim 3 wherein said R comprises a polar group selected from the group consisting of carbonyl, hydroxyl, and carbamoyl.

6. The composition of claim 3 wherein said fluoroaliphatic radical-containing piperazine compound is

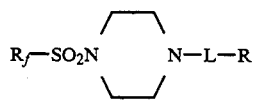

where $R_f$ is a fluorinated, monovalent, saturated aliphatic radical of at least two fully fluorinated carbon atoms, L is a divalent polar-moiety, and R is an organic moiety comprising from 4 to 35 carbon atoms.

7. The composition of claim 6 wherein said divalent polar-moiety is selected from the group consisting of —C(O)—, —CONR—, —$CH_2CR(OH)$—, or combinations thereof, where R is H or lower alkyl containing 1 to 6 carbon atoms.

8. The composition of claim 7 wherein said $R_f$ is $C_nF_{2n+1}$, where n is from 5 to 20, and said R is a non-polar moiety comprising an aryl moiety, alkyl moiety, or combinations thereof.

9. The composition of claim 8 wherein said R is an alkyl group of formula $C_yH_{2y+1}$, where y is from 4 to 20.

10. The composition of claim 9 wherein said Q is —$SO_2$—.

11. The composition of claim 1 wherein said polymer is polyamide, polyester, polyurethane, or polyolefin.

12. A shaped article comprising the composition of claim 1.

13. Fiber comprising the composition of claim 1, said fiber being oil and water repellent.

14. Fiber of claim 13 wherein said fibers are blown microfibers.

15. Fibers of claim 13 wherein said fibers are in the form of carpet yarn.

16. Fiber of claim 13 having a fluorine content in the range of about 100 to 10,000 ppm based on the weight of the fiber.

17. Film comprising the composition of claim 1, said fiber being oil and water repellent.

18. Film of claim 17 having a fluorine content in the range of about 100 to 10,000 ppm based on the weight of the fiber.

* * * * *